(12) United States Patent
Zhang et al.

(10) Patent No.: US 6,344,219 B1
(45) Date of Patent: Feb. 5, 2002

(54) CHINESE DRUG COMPOSITION FOR TREATMENT OF PEPTIC ULCER AND PREPARATION THEREOF

(76) Inventors: Yongchuan Zhang, Block A, 12F-Guomao Dasha, Hubinnanlu, Xiamen, Fujian 361004; Wendi Chen, 10-2 Changgujie, Zhenhailu, Xiamen, Fujian 361003; Yuyao Chen, 504 Guoshuijushuselou, 91 Chengxilu, Datongzheng, Tong-an County, Xiamen, Fujian 361000, all of (CN)

( * ) Notice: Subject to any disclaimer, the term of this patent is extended or adjusted under 35 U.S.C. 154(b) by 0 days.

(21) Appl. No.: 08/913,946

(22) PCT Filed: Mar. 25, 1996

(86) PCT No.: PCT/CN96/00020

§ 371 Date: Oct. 26, 1998

§ 102(e) Date: Oct. 26, 1998

(87) PCT Pub. No.: WO96/29084

PCT Pub. Date: Sep. 26, 1996

(30) Foreign Application Priority Data

Mar. 23, 1995 (CN) ............................................ 95114819

(51) Int. Cl.$^7$ ...................... A61K 35/78; A61K 39/385; A61K 9/28
(52) U.S. Cl. ...................... 424/725; 424/774; 424/779; 424/474; 514/925
(58) Field of Search ................................ 424/725, 774, 424/779, 404, 474; 514/925

(56) References Cited

U.S. PATENT DOCUMENTS 5,290,557 A * 3/1994 Mason et al.
5,888,984 A * 3/1999 Brown

FOREIGN PATENT DOCUMENTS

CN 1104098 A * 6/1995

OTHER PUBLICATIONS

Lewis, W. H., Medical Botany: Plants affecting man's health. John Wiley & Sons, Inc., USA, pp. 291–292, 1977.*

Franca et al., Revista da Sociedade Brasileira de Medicina Tropical, 29(3): 229–232. Plants used in the treatment of leishmanial ulcers due to Leishmania (Viannia) braziliensis in an endemic area of Bahia, Brazil, 1996.*

Encyclopedia of Chinese Medicine, Shanghai Science and Technology Publication)—pp. 90–91 and 527 (1986).

Takagi K., et al. Japan J Pharmacol 1968, 18:9–18.

Takagi K., et al. Japan J Pharmacol 1969, 19:418–426.

Okabe S., et al. Am J Dig Dis, 16(3): 277–284, 1971; and.

Zhang et al. ACTA Pharmaceutica Sinica 1984, 19 (1) : 5–11 and its abstract in English.

A Simple Method for the Uniform Production of Gastric Ulceration in the Rat, Shay, et al. 1943, pp. 43–61.

\* cited by examiner

*Primary Examiner*—Christopher R. Tate
*Assistant Examiner*—Michele C. Flood
(74) *Attorney, Agent, or Firm*—Fulbright & Jaworski L.L.P

(57) ABSTRACT

The present invention provides a Chinese drug composition for the treatment of peptic ulcer comprising oil of *Chenopodium ambrosiodes* and oil of *Adina pilulifera* in a ratio of 18–70:0.5–5 by weight and preparation thereof. The Chinese drug composition possesses therapeutic effect on peptic ulcer to mammal animals including human, and intensely inhibits pyloric spirillum.

10 Claims, No Drawings

CHINESE DRUG COMPOSITION FOR TREATMENT OF PEPTIC ULCER AND PREPARATION THEREOF

FIELD OF THE INVENTION

The present invention is related to the drug for the treatment of gastric disease especially to a Chinese drug composition for the treatment of peptic ulcer and preparation thereof.

BACKGROUND OF THE INVENTION

Peptic ulcer is a common, frequently-occurring disease with high incidence. The aim of the therapy of peptic ulcer is to eliminate symptoms, promote healing, and to prevent relapse and complications. At present the medicines used in the treatment of peptic ulcer still do not meet the therapeutical demands. The drugs utilizing in the treatment of peptic ulcer at present are all exiting the defects of expensive price, obvious side effects, and high relapse.

In Chinese medicine, peptic ulcer related to the categories of "epigastric pain", "stomachache caused by the dominant liver-energy" and so on. The mechanism of the disease mostly is concerned with the deficiency of qi in the spleen and stomach, or the stagnation of vital energy caused by cold-evil, or the obstruction of the stomach caused by damp-heat, or the internal stagnation of the blood and so on. The hindrance of functional activities of qi yields the pain, and the stagnation of qi leads to blood stasis, or prolonged diseases involves the collateral, the prolonged blood stasis in the interior changes into heat then the flesh was rotted and the muscles was injured and the ulcer was formed. "NeiJing SuWen: JuTongLun (Plain Question of Canon of Internal Medicine: On the Pain)": "the cold-evil accumulated between the stomach and intestinal under the half-superficies and half-interior position so that pain was formed due to the blood failed to circulate and the small collateral was blocked", "the cold-evil accumulated in the stomach and intestinal adversely evolved from upside resulted in pain and vomit". In clinics, many cases were categorized in cold-evil accumulating in stomach, stagnation of qi leads to blood stasis, Ye Tian-shi of Qing dynasty gave a brilliant exposition on the therapeutical method: "What is the essential of (stomach disease)! The beginning of the disease mentioned above is occurred at the channel then goes into the collateral as a result of prolonged pain, channel is the principal pathogeny and collateral controls the blood, therefore the treatment of qi and blood is abundantly clear". ("Lin Zheng Zhi Nan Yi An, Wei Wan Tong (Medical Record Guides of clinical Symptoms Epigastric pain)"). Li Donghuan pointed out in "Nei Wei Shang Pian Huo Lun, Fei Shi Pi Wei Xu Fang (On the recognition of the Nature of internal and traumatic injuries, Formula of the deficiency of Spleen and Stomach due to Lung)". "Fire has been exhausted and can not be transported and transformed, in addition of the invasion by cold-evil, all of this accumulated as fullness pain. Dispelled it with pungent hot medicine and associated with sweet-bitter ones to use bland flavor drug for clearing up then qi become gentle and stomach become harmony, as a result the pain would be relieved".

At present, using the drug prepared from two kinds of Chinese medicine indicated as follow for the treatment of peptic ulcer still has not been reported. This two kinds of medicine are:

*Chenopodium ambrosioides* (cf. Du Yao Ben Cao (poison Herbs) ed. by Yang Lun-liang pp 925–927. China Chinese Medicine Publish House, Dec. 1993): *Chenopodium ambrosioides* is the total herb with the ear of fruit of the plant of *Chenopodiaceae chenopodium ambrosioides* L. The essential oil (oil of *Chenopodium ambrosiodes*) contained in the total herb is 0.4–1% composing mainly of Ascaridole, p-Cymene, and other terpeniod such as aritasone, limonese etc. possesses the activities of dispelling wind-evil, killing germs, inducing menstruation and relieving pain.

*Adina pilulifera* (cf. Zhong Hua Yao Hai (Chinese Medicine Dictionary) ed. by Ran Xian-de p426, Harbin Publish House, Aug. 1993); It is a plant of Rubiaceae, the scientific name is *Adina pilulifera* (Lam Franch). Its leaves contain the admixture of acidic saponin which gave quinovic acid and acetate thereof aftwr hydrolysis, it also contains beta-sitosterol, and its stern contains quinovic acid, beta-sitosterol and the admixture of saponin which yields quinovic acid, betulic acid and cinchoninic acid after hydrolisis. The fraction of saccharide contains mainly glucuronate. It exhibits the effect of clearing away heat and dampness, removing blood stasis and relieving pain, arresting blood and promoting the regeneration of tissues and so on.

The object of the invention is to overcome the deficiency of the prior art and to provide a Chinese drug composition comprising mainly of the active components of *chenopodium ambrosioides* and *adina pilulifera* for the treatment of peptic ulcer.

The another object of the present invention is to provide a method for preparing said Chinese drug composition.

The still another object of the present invention is to provide a capsule preparation comprising said Chinese drug composition.

The further object of the present invention is to provide a use of said Chinese drug composition in the preparation of drug for the treatment of peptic ulcer.

SUMMARY OF THE INVENTION

The present invention provides a Chinese drug composition for the treatment of peptic ulcer which comprises the oil of *Chenopodium abrosioides* and the oil of *Adina pilulifera*, in a ratio of oil of *Chenopodium ambrosiodes*: oil of *Adina pilulifera* being 18–70:0.5–5 (by weight).

The Chinese drug composition of this invention was prepared according to the following procedure, that is:

*Chenopodium ambrosioides* and *Adina pilulifera* (50–70:30–50 by weight) were steam distilled for extracting the essential oil, and collecting the oil obtained.

The preparation containing the Chinese drug composition of this invention can be administered with any oral preparations preferable is capsules, its preparative method may be the regular method known in the existing art.

The Chinese drug composition of present invention possesses good therapeutic effect on peptic ulcer and is provided with significant inhibitory action to pyloric spirillum.

DETAILED DESCRIPTION OF THE INVENTION

The Chinese drug composition of this invention is the active components extracted from *Chenopodium ambrosioides* (Chenopodiaceae) and *Adina pilulifera* (Rubiaceae) which were the essential oils obtained by steam distillation of *Chenopodium ambrosioides* and *Adina pilulifera* in a ratio of 50–70:30–50 by weight. The essential oil obtained was a mixture comprising the oil of *Chenopodium ambrosioides* and oil of *Adina pilulifera* oil of *Chenopodium ambrosioides*: oil of *Adina pilulifera* therein is 18–70:0.5–5 (by weight).

The source of the medicines of this invention is spread in everywhere, and the price of the medicines is cheap. The preparative procedure is simple and easy to conduct which is advantageous to decrease the product cost.

The results of animal tests indicated that the Chinese drug composition of present invention possesses good protective effect to the ulcer of stress, pyloric ligation, acetic acid burn, and Reserpine, Indomethacin and Histamine induced peptic ulcer (details are shown in experiments 1–1 to 1–6 thereinafter).

The generally accepted mechanism of peptic ulcer was the "balance theory" suggested by Shay which meant that the defending factors and the attacking factors were in a state of imbalance. Anti-ulcer agents showed the therapeutic effect through promoting the defending factors or by retarding the attacking factors.

The stress ulcer is generally considered as an acute ulcer caused by the disorder of central nerve system and automatic nerve system function and the disorder of gastrointestinal peristalsis and secretion.

The mechanism of pyloric ligation ulcer is considered to be the result of the accumulation of acid and pepsin. The ulcer induced by Reserpine is related to the stimulation of vagus and the increase of gastric secretion.

The increased secretion of gastric juice with high acidity induced by Histamine is probably an important factor of ulcer occurrence. The medicine of the present invention possesses significant inhibition to the four kinds of acute gastric ulcer mentioned thereinbefore and associated with the effects of decreasing secretion and inhibition of the gastric acid and pepsin activity. All of these indicated that retarding the attacking factors is one of its anti-ulcer mechanism.

Indomethacin decreases the amount of prostaglandin which possesses potent cell protection effect in gastric mucosa by inhibiting cyclooxygenase in the mucosa and interfering biosynthesis of prostaglandin, thus affected the mucosal epitheliosis, mucus formation and the blood supply in mucosa resulted in retarding the defending ability and leaded to the occurrence of ulcer.

The medicine of this invention can effectively inhibit the ulcer induced by Indomethacin. The determination of the Alcian blue absorption by the binding mucus of stomach wall indicated that the another mechanism of the medicine is to promote the synthesis of gastric mucus and enhance the defending ability of gastric mucosa.

Ulcer caused by acetic acid is a model of chronic ulcer. Its characterization is similar to the human peptic ulcer, with prolonged healing duration, and is a kind of chronic obstinate ulcer. The medicine of this invention can significantly decrease the ulcer volume burned by acetic acid indicating that it has the effect of promoting the healing.

Pyloric spirillum is closely related with chronic gastritis, gastric and duodenal ulcer, and the relapse of the ulcer hence was increasingly taken seriously. The inhibitory test in vitro to pyloric spirillum showed that the medicine of the present invention possesses drastic inhibitory activity. MIC of this medicine is 0.024–0.048 mg/ml. According to the dose used in clinical trial (each time 100 mg) concentration of the medicine in the gastric juice is far exceeded MIC. This is the another therapeutic mechanism of the medicine of the present invention for the treatment of peptic ulcer.

In addition, the medicine of the present invention shows drastic inhibitory activity to gastrointestinal peristalsis, and antagonizes Ach, $BaCl_2$, His against agonization on gut. The antispastic action on gastrointestina smooth muscle can relieve pain caused by the ulceration of upper digestive tract.

The results of clinical application to 633 patients suffering peptic ulcer showed that the total effective rate is 95.26% and the cure rate is 80.88%.

The therapeutic effect of the medicine of this invention is better than that of single Chinese drug. The water decocted preparation of *Chenopodium ambrosioides* and *Adina pilulifera* which was prescribed according to the ratio thereinbefore in still efficacious. The effective rate of 960 clinical cases is 75% and the cure rate is 62%.

It is obvious that the medicine of this invention possesses significant therapeutic effect to peptic ulcer.

*Chenopodium ambrosioides* comprised in the medicine of present invention possesses definite toxicity. The results of its acute toxic test is:

$LD_{50}$ (ig)=93.1 mg/kg $LD_{95}$=93.1±18.5 mg/kg (74.5–111.5 mg/kg)

The results of long term toxic test is identical with that of *Chenopodium ambrosioides*. The employed dose of the drug of this invention should be less than the toxic dose.

The dose of the medicine of present invention used in clinic is generally about 300 mg/day, preferably is about 240 mg/day.

Excepting the preparation of capsule described in this text, the drug of present invention can be prepared into any suitable dosage forms, such as capsules. Owing to the specific odor of the essential oils, preparation of capsule is preferred. Its preparative method is the regular procedure known in the art, the preferable method is: vegetable oil was added to the extracted essential oil for dilution to prepare the material oil. The vegetable oils used for dilution are pharmaceutically acceptable, for example, peanut oil rapeseed oil, and the purified vegetable oils, such as to remove the solid fat at about 0° C. is more preferred. Medical gelatin and appropriate amount of medical glycerol were dissolved in distilled water and filtrated to give the gelatin solution. Material oil and gelatin oil were put into the capsule-making-machine and were dropped into capsules. After setting, drying, washing, sterilizing, sorting out, and packing of the prepared capsules the capsules of the drug of this invention were obtained.

DETAILED DESCRIPTION OF THE PREFERRED EMBODIMENTS

The drug of present invention was further described through the following examples and experiments.

EXAMPLE 1

Stern and leaves of *Chenopodium ambrosioides* 600 g and stern and leaves of *Adina pilulifera* 400 g were put into the distillator and were steam distilled for extracting the essential oils, i.e. the mixture of oil of *Chenopodium ambrosioides* and oil of *Adina pilulifera*, to give 2.4 g essential oil.

EXAMPLE 2

Stern and leaves of *Chenopodium ambrosioides* 500 g and stern and leaves of *Adina pilulifera* 500 g were put into the distillator and were steam distilled for extracting the essential oils, i.e. the mixture of oil *Chenopodium ambrosioides* and oil of *Adina pilulifera*, to give 2.1 g essential oil.

EXAMPLE 3

Stern and leaves of *Chenopodium ambrosioides* 700 g and stern and leaves of *Adina pilulifera* 300 g were put into the distillator and were steam distilled for extracting the essential oils, i.e. the mixture of oil *Chenopodium ambrosioides* and oil of *Adina pilulifera*, to give 2.9 g essential oil.

EXAMPLE 4

Peanut oil(removing solid fat at about 0° C.) was added to the mixture of oils obtained from Example 1 to dissolve and dilute the material oil. Medical gelatin and appropriate amount of glycerol were dissolved in distilled water at about 70° C. and filtrated to give gelatin solution with appropriate concentration. The obtained material oil and gelatin oil were put into the capsule-making-machine and were dropped into capsules of the weight 100 mg containing the oil of *Chenopodium ambrosioides* about 50 mg and the oil of *Adina pilulifera* about 1 mg in each capsule. After setting, drying, washing, sterilizing, and sorting out the produced capsules were packed.

EXAMPLE 5

Peanut oil (removing solid fat at about 0° C.) was added to the mixture of oils obtained from Example 2 to dissolve and dilute the material oil. Medical gelatin and appropriate amount of medical glycerol were dissolved in distilled water at about 60° C. and filtrated to give gelatin solution with appropriate concentration. The obtained material oil and gelatin oil were put into the capsule making machine and were dropped into capsules of the weight 80 mg containing the oil of *Chenopodium ambrosioides* about 39 mg and the oil of *Adina pilulifera* about 1 mg in each capsule. After setting, drying, washing, sterilizing and sorting out the produced capsules were packed.

Pharmacodynamic experiments

Experiment 1

1-0. Materials

I. Medicines (1). Medicine of present invention i.e. the mixed essential oils obtained from Example 1 thereinbefore was diluted with purified vegetable oil resulting in the drug in which the content of essential oils is about 520 mg/g.

(2). Ranitidine hydrochloride, manufactured by Bai Yun Shan Pharmaceutical Factory, Guangzhou.

(3). Atropine sulfate (powder), manufactured by Beijing Pharmaceutical Factory.

(4). Indomethacin (powder), manufactured by Beijing Third Pharmaceutical Factory.

(5). Sodium deoxycholate, repacking imported product of Serva.

(6). Histamine phosphate (powder) manufactured by Shanghai Institute of Biochemistry, Chinese Academy of Sciences.

(7). Alcian blue 8Gs, repacking imported product of Chroma.

(8). Acetyl choline chloride, manufactured by Shanghai Chemical Reagent General Factory (Third Factory).

II. Animals (1) Rats(SD), weight 150–220 g, the weight difference is not exceeded to 40 g in a same experiment.

(2) Mice(ICR), weight 18–22 g, the weight difference is not exceeded to 4 g in a same experiment.

All the above animals used in the experiments are provided by China-Great Britain joint Enterprise Shanghai SIPPR/BK Lje.

1-1. The effect to stress ulcer

The model was established following Takagi's method. Takagi, et al., The Effects of Drugs on the production and Recovery Processes of the Stress Ulcer, 18:9–18 (1968); and Takagi et al., A New Method For The Production of Chronic Gastric Ulcer in Rats and The Effect of Several Drugs on its Healing, Japan J. Pharmacol Japan J. Pharmacol 19:418–426 (1969). Fifty rats, 159+13 g, male and female half and half, were randomly divided into five groups according to sex and weight and were administered with drugs daily twice, once both in the morning and afternoon for two days. From the beginning of the experiments, food was abstained but water was freely fed. One hour after the last administration, rats were bound on a board and were soaked in a thermostatic flowing water bath at 21$\underline{34}$1° C. for 18 hr then were executed by decapitation. Take out the stomach by abdominal section and ligate the pylorus first then inject 10 ml of 1% formaldehyde solution through cardia of stomach and ligate the cardia. After formalizing the stomach in 1% formaldehyde solution for 10 min, the stomach was cut along the greater curvature with scissor, rinse with normal saline solution for three times and absorb with filter paper, then flatten it on a glass plate and examine the degree of mucosa ulcer and count the number using magnifier. Calculate the ulcer index following Okabe's Method and the results were shown in Table 1. The drug of present invention used in this experiment is the diluted essential oil obtained from Example 1.

TABLE 1

Effect to stress ulcer

| Group | Number of animal | Dose (mg/kg × 2) | Ulcer index (x ± SD) | Rate of inhibition (%) | P value |
|---|---|---|---|---|---|
| 1. Control normal saline | 10 | 10 ml bid × 2 | 3.66 ± 1.33 | | |
| 2. Group 1 of the present invention | 10 | 5, bid × 2 | 1.79 ± 1.29 | 51.1 | <0.01 |
| 3. Group 2 of the present invention | 10 | 10, bid × 2 | 1.15 ± 0.91 | 68.6 | <0.001 |
| 4. Group 3 of the present invention | 10 | 15, bid × 2 | 0.99 ± 1.10 | 73.0 | <0.001 |
| 5. Ranitidine | 10 | 100, qd × 2 | 2.14 ± 0.46 | 41.5 | <0.02 |

The results of Table 1 showed that the drug of present invention can significantly inhibit the formation of stress ulcer of rats induced by water soaking. The effect is dose dependance.

1-2. Effect to the ulcer of pyloric ligation

The experiment is conducted following Shay's method. Fifty rats, 190+20 g, male and female half and half, were randomly divided into five groups according to weight and sex and were administered as 1-1 for three days. Food was abstained but water was freely fed before 48 hr of the operation. After 2 hr of the last administration, operation of pyloric ligation was conducted then both food and water were abstained. After 48 hr the rats were executed and their gastric juice was collected for measuring the volume, and determining the free acid, total acid and pepsin following Metle's method. Ulcer index was examined as 1-1 and the results were shown in Table 2.

TABLE 2

Effect to the ulcer of pyloric ligation

| Group | | | | | | | |
|---|---|---|---|---|---|---|---|
| 1. Control (normal saline) | 10 | 10 ml | 4.04 ± 2.02 | 44.3 ± 18.0 | 12.54 ± 18.0 | 7.72 ± 1.37 | 176 ± 60 |
| 2. Group 1 of the invention | 10 | 5.0 | 1.32 ± 1.06** | 40.7 ± 12.5 | 40.7 ± 12.5 | 8.80 ± 2.17 | 156 ± 89 |
| 3. Group 2 of the invention | 10 | 10.0 | 1.13 ± 0.65*** | 28.6 ± 9.6** | 28.6 ± 9.6** | 2.70 ± 1.89*** | 155 ± 59 |
| 4. Group 3 of the invention | 10 | 15.0 | 0.50 ± 0.28*** | 25.4 ± 6.9** | 25.4 ± 6.9** | 2.52 ± 1.17*** | 126 ± 44* |
| 5. Ranitidine | 10 | 200 | 1.22 ± 1.44** | 28.9 ± 12.4** | 28.9 ± 12.4** | 1.84 ± 2.35*** | |

Compare with control
*P < 0.05,
**P < 0.01,
***P < 0.001

The drug of present invention can inhibit the formation of pyloric ligation ulcer. The amount, total acid and free acid of gastric juice of the group administrated with the dose of 10–15 mg/kg were decreased and the activity of pepsin was also decreased for the group administered with the dose of 15 mg/kg.

1-3. Effect to the model of chronic gastric ulcer of rats caused by acetic acid burn The experiment was conducted using adapted Takagi's method. Fifty rats, 165+15 g, male and female half and half, after abstaining food without abstaining water for 24 hr, were primary anesthetized with ether and their skin were sterilized as regular method. After abdominal section the stomach was gently pulled out. A small glass tube with 0.5 cm inner diameter and 3 cm length was inserted into the stomach near the lesser curvature stomach gland of pylorus using middle finger to resist against the opposite stomach wall. 0.1 ml acetic acid was injected into stomach through the glass tube. After 30 sec counting with stopwatch, acetic acid was sucked out and the stomach was rinsed with sterilized normal saline for three times. Remove out the glass tube and absorb the normal saline on its external surface with sterilized filter paper the stomach was put into the abdomen then sew up the wound and sterilize. The rats was randomly divided into 5 groups according to sex and weight on the second day of operation. The rats were administered with drug ig qd×12 day, after abstaining food overnight then were executed by decapitation. The ulcer volumes were measured using the method of injection ink with a micro syringe. The results were shown in Table 3.

TABLE 3

Effect to the model of chronic gastric ulcer of rats caused by acetic acid burn

| Group | No. of animal | dose (mg/kg × day) | ulcer volume (μl, x ± SD) | rate of inhibition (%) | P value |
|---|---|---|---|---|---|
| 1. N.S. | 10 | 10 ml × 12 | 3.49 ± 1.64 | | |
| 2. Group 1 of the invention | 10 | 10 × 12 | 1.99 ± 1.16 | 43.0 | <0.05 |
| 3. Group 2 of the invention | 10 | 14 × 12 | 1.87 ± 1.44 | 46.4 | <0.05 |
| 4. Group 3 of the invention | 10 | 20 × 12 | 1.40 ± 1.80 | 59.9 | <0.05 |
| 5. Ranitidine | 10 | 200 × 12 | 1.72 ± 1.46 | 50.7 | <0.05 |

The significant decrease of the ulcer volume by the drug of present invention indicated that this drug possesses the action of promoting the recovery of ulcer.

1-4. Effect to the ulcer of rats induced by Reserpine

Fifty rats, 180±18 g, male and female half and half, were divided into five groups and were treated with drug ig once daily for three days. After abstaining food for 24 hr Reserpine 5 mg/kg was injected subcutaneously. The rats were executed by decapitation after 18 hr and the gastric ulcer was examined as the same method of 1-1. The results were shown in Table 4.

TABLE 4

Effect to gastric ulcer of rats induced by Reserpine

| Group | No. of animal | dose (mg/kg) | ulcer index (x ± SD) | rate of inhibition (%) | P value |
|---|---|---|---|---|---|
| 1. N.S. | 10 | 10 ml | 34.8 ± 12.5 | | |
| 2. Group 1 of the invention | 10 | 5.0 | 20.6 ± 5.9 | 40.8 | <0.02 |
| 3. Group 2 of the invention | 10 | 10.0 | 14.2 ± 2.2 | 59.2 | <0.001 |
| 4. Group 3 of the invention | 10 | 20.0 | 7.0 ± 2.5 | 79.9 | <0.001 |
| 5. Ranitidine | 10 | 200.0 | 7.6 ± 2.0 | 78.2 | <0.001 |

The results showed that the drug of present invention possesses very significant inhibitory effect to the gastric ulcer induced by Reserpine. Its effect is dose dependence. The dose of 20 mg/kg of this drug is as effective as that of 200 mg Ranitidine.

1-5. Effect to gastric ulcer of rats induced by Indomethancin

Forty two rats, 162±14 g, male and female half and half, the groups of administration were treated with drug ig in the morning everday for 3 days to establish the model following Zhang's method Zhang et al. Acta Pharmaceutica Sinica, 19(1):5–11 (1984), after 0.5 hr of the last administration ip 40 mg/kg of Indomethacin and ig 30 mg/kg of sodium deoxycholate 5 hr later the rats were executed. The gastric mucosa damage index was examined with the same method of 1-1, then stomachs were put into 0.2% Alcian blue solution to soak for 19 hr (25° C.). The soaked solution was centrifuged at 3000 rpm for 20 min, the absorbance of supernatant was determined using 721 model spectrophotometer at 615 nm. The results were shown in Table 5.

TABLE 5

Effect to gastric ulcer induced by Indomethacin

| Group | No of animal | dose (mg/kg) | ulcer index (x ± SD) | inhibition rate (%) | absorbance (x ± SD) | inhibition rate (%) |
|---|---|---|---|---|---|---|
| 1. Control N.S. | 10 | 10 ml × 3 | 37 ± 13 | | 0.193 ± 0.039 | |
| 2. Group 1 of the invention | 8 | 5.0 × 3 | 6.5 ± 6.7** | 82.4 | 0.122 ± 0.043** | 3.68 |
| 3. Group 2 of the invention | 8 | 10.0 × 3 | 4.4 ± 3.7*** | 88.1 | 0.117 ± 0.039** | 39.4 |
| 4. Group 3 of the invention | 8 | 20.0 × 3 | 2.6 ± 3.0*** | 93.0 | 0.106 ± 0.025*** | 45.1 |
| 5. Atropine | 8 | 10 × 1 | 1.0 ± 1.3 | 97.3 | 0.082 ± 0.024*** | 57.5 |

It is obvious from the results of the experiment that the drug of present invention can significantly inhibit the formation of gastric ulcer induced by Indomethacin and can increase the secretion of the binding mucus of stomach wall.

1-6. Effect to ulcer of mice induced by Histamine

Forty mice, male 23±2 g, were divided into five groups, and were administrated once both in the morning and afternoon of everyday by ig. Mice were abstained to feed food for 24 hr except water, then administered Histamine 80 mg/kg, ip, after abstaining food for 8 hr were executed. Take out the stomachs and examine ulcer index using the same method as 1-1. Results were shown in Table 6.

TABLE 6

Effect to ulcer of mice induced by Histamine

| Group | No. of animal | dose (mg/kg × 2) | ulcer index (x ± SD) | rate of inhibition (%) | P value |
|---|---|---|---|---|---|
| 1. N.S. | 10 | 10 ml × 2 | 11.5 ± 7.1 | | |
| 2. Group 1 of the invention | 10 | 10 bid × 2 | 5.2 ± 4.5 | 54.8 | <0.05 |
| 3. Group 2 of the invention | 10 | 20 bid × 2 | 3.1 ± 3.7 | 73.0 | <0.01 |
| 4. Ranitidine | 10 | 200 bid × 2 | 1.4 ± 3.5 | 87.8 | <0.001 |

The above results indicated that the drug of present invention can significantly inhibit the formation of ulcer induced by ip Histamine.

Experiment 2

Test of the inhibitory effect to pyloric spirillium in vitro 2-0. Materials

1. Drug of present invention i.e. mixed essential oils prepared from practice example 2 thereinbefore and diluted with purified vegetable oil in which the content of essential oil is 0.97 mg/ml.

2. Bacterium lines: Six lines of HP with typical characterization were newly isolated from the gatric mucosa of the patient suffering chronic gastritis and were cultured. The cultured bacteria were reproduced on the solid culture medium for 48 hr and were used for inhibitory test.

2-1. Method

Agar dilution method was used. Egg yolk was used in the drug emulsifying agent. The emulsified solution was multiply diluted with sterilized distilled water and was mixed with culture medium then was poured into the culture plate. Bacterium was scraped from the solid culture medium for ¼ ring with the ring of platinum wire and was cultured on the culture plate. After culturing at 37 C. under slight oxygen atmosphere (5%, $O_2$, 10% $CO_2$, 85% $N_2$) for 72 hr the results were examined. The lowest concentration contained in the plate without growing HP was considered to be the minimum inhibitory concentration (MIC).

2-2 Results

The growing circumstances of HP were shown in the following Table, in which "+" means growing, "-" means ingrowing.

TABLE 7

Results of the inhibition to pyloric spirilium

| bacterium line | drug concentration (mg/ml) | | | | | | | | | | | |
|---|---|---|---|---|---|---|---|---|---|---|---|---|
| | 24.8 | 12.4 | 6.2 | 3.1 | 1.55 | 0.78 | 0.38 | 0.194 | 0.048 | 0.024 | 0.012 | 0 |
| 92031 | − | − | − | − | − | − | − | − | − | + | + | + |
| 92082 | − | − | − | − | − | − | − | − | − | − | + | + |
| 92083 | − | − | − | − | − | − | − | − | − | + | + | + |
| 92084 | − | − | − | − | − | − | − | − | − | − | + | + |
| 92085 | − | − | − | − | − | − | − | − | − | + | + | + |
| 92086 | − | − | − | − | − | − | − | − | − | − | + | + |

Experiments indicated that 6 HP lines all can not grow on the culture medium containing the drug of present invention of 0.048 ug/ml concentration 3 of 6 HP lines cannot grow on the culture medium containing the drug of 0.024 ug/ml concentration 0.012 ug/ml and less concentration of this drug can not inhabit the growing of all the 6 HP lines.

Therefore the MIC of this drug is 0.024 ug/ml–0.048 ug/ml. This indicated that the drug of present invention possesses drastic inhibitory effect to pyloric spirillum.

Experiment 3

3-1. Cases

Among 633 cases the ratio of men and women is 5.1:1.9, the oldest age is 79 and the youngest age is 17. Statistic of the cases according to ages are: age of 10–20 is 31 cases, age of 21–30 is 281 cases, age of 31–40 is 228, age of 41–50 is 78 cases age of 51–60 is 43 cases, age of 61–70 is 14 cases, and age of 71–80 is 11 cases.

Classification according to pathology: duodenum ulcer is 422 cases (66.7%), gastric ulcer is 182 cases (28.75%), complex ulcer is 29 cases (4.68%). Classification according to the course of disease: less than half year is 15 cases (2.37%). ½—1 year is 46 cases (7.27%), 2–5 year is 291 cases (45.97%), 6–10 year is 158 cases (24.95%), more than 10 year is 74 cases (11.69%), and the unknown course of disease is 49 cases (7.74%).

3-2 Therapeutical method

The patients mentioned hereinabove were administered with 3 capsules prepared in Example 5 thereinbefore everyday. The dose of each time is 80 mg. Successive 4 weeks is one course of treatment.

3-3. Results

The results of clinical symptom and Barium meal check showed that 512 cases were cured (80.88%), 91 cases were efficacious (14.38%), 30 cases were failed (4.74%). The total efficacious number was 603 cases and the total effective rate was 95.26%.

Industrial Application

The Chinese drug composition of present invention can be manufactured for preparing the medicine for the treatment of peptic ulcer.

We claim:

1. A composition for the treatment of peptic ulcer comprising oil of *Chenopodium ambrosiodes* and oil of *Adina pilulifera* in a ratio of 18–70:0.5–5 by weight.

2. A method for preparing a composition for the treatment of peptic ulcer comprising the steps of: steam distilling at least one of the members selected from the group consisting of stems and leaves of each of *Chenopodium ambrosioides* and *Adina pilulifera* in a ratio of 50–70:30–50 by weight to extract the essential oils thereof; and collecting the essential oils.

3. A composition prepared by the process of steam distilling at least one of the members selected from the group consisting of stems and leaves of each of *Chenopodium ambrosioides* and *Adina pilulifera* in a ratio of 50–70:30–50 by weight to extract the essential oils thereof; and collecting the essential oils.

4. A pharmaceutical preparation comprising the drug composition according to claim 1.

5. The pharmaceutical preparation of claim 4, wherein the pharmaceutical preparation is in the form of a capsule.

6. A method of treating peptic ulcers comprising administering to a subject in need thereof a therapeutically effective amount of the composition of claim 1.

7. The method of claim 6, wherein the subject is a mammal.

8. The method of claim 6, wherein the subject is a human.

9. The method of inhibiting pyloric spirrillum of mammals, comprising administering a spirillum inhibiting amount of the composition of claim 1 to mammal in need thereof.

10. The method of claim 9, wherein said mammal is a human.

\* \* \* \* \*